United States Patent
Hartle et al.

(10) Patent No.: US 6,706,904 B1
(45) Date of Patent: Mar. 16, 2004

(54) DIMETALHYDROXY MALATES

(75) Inventors: Jennifer Hartle, Harrisville, UT (US); Stephen D. Ashmead, Clinton, UT (US); Robert Kreitlow, Roy, UT (US)

(73) Assignee: Albion International, Inc., Clearfield, UT (US)

( * ) Notice: Subject to any disclaimer, the term of this patent is extended or adjusted under 35 U.S.C. 154(b) by 0 days.

(21) Appl. No.: 10/310,108

(22) Filed: Dec. 4, 2002

(51) Int. Cl.[7] .................. A23K 1/175; C07F 13/00; C07F 1/08; C07F 3/06; C07F 15/02
(52) U.S. Cl. .............. 556/5; 556/114; 556/138; 556/147; 556/28; 562/582; 426/74
(58) Field of Search .......... 556/49, 114, 133, 556/147, 28; 562/582; 426/74

(56) References Cited

U.S. PATENT DOCUMENTS

| | | | |
|---|---|---|---|
| 4,461,778 A | 7/1984 | Vialatte nee Geolier | 426/422 |
| 4,830,862 A | 5/1989 | Braun et al. | 426/74 |
| 5,068,421 A | 11/1991 | Horng | 562/583 |
| 5,186,965 A | 2/1993 | Fox et al. | 426/74 |
| 5,298,634 A | 3/1994 | Connor et al. | 549/485 |
| 5,389,387 A | 2/1995 | Zuniga et al. | 426/74 |
| 5,401,524 A | 3/1995 | Burkes et al. | 426/590 |
| 5,422,128 A | 6/1995 | Burkes et al. | 426/74 |
| 6,294,207 B1 | 9/2001 | Christiansen et al. | 426/74 |

OTHER PUBLICATIONS

Abstract: Henry MH and GM Pesti, *An Investigation of Calcium Citrate–malate as a Calcium Source for Young Broiler Chicks*, Poult Sci Aug. 2002;81(8):1149–55.

Abstract: Mithieux G, FV Vega, and JP Riou, *The Liver Glucose–6–phosphatase of Intact Microsomes is Inhibited and Displays Signoid Kinetics in the Presence of Alpha–ketoglutarate–magnesium and Oxalpacetate–magnesium Chelates*, J Biol Chem Nov. 25, 1990;265(33): 20364–8.

Primary Examiner—Porifirio Nazario-Gonzalez
(74) Attorney, Agent, or Firm—Thorpe North & Western, LLP

(57) ABSTRACT

Dimetalhydroxy malate compositions as well as methods of administering and making such bioavailable compositions are provided. The metal used can be any nutritionally relevant divalent metal such as calcium, magnesium, zinc, copper, manganese, and iron. The composition can be prepared by reacting malic acid with a divalent metal oxide or hydroxide at a 1:2 molar ratio. The composition can be administered to a warm-blooded animal by any of a number of known delivery routes, including oral delivery.

26 Claims, No Drawings

DIMETALHYDROXY MALATES

FIELD OF THE INVENTION

The present invention is drawn to compositions, and methods of making and administering compositions, that can be used for mineral supplementation. More specifically, the present invention is drawn to dimetalhydroxy malates.

BACKGROUND OF THE INVENTION

Magnesium is a mineral that is needed in humans and other warm-blooded animals for bone, protein, and fatty acid formation. Magnesium is also involved in the formation of new cells, activating certain vitamins, relaxing muscles, clotting blood, and forming ATP. People with diabetes often have magnesium levels that are lower than normal compared with those who have normal glucose tolerance. Supplementation of magnesium can help maintain health in some of these areas, as well as help in overcoming some of these problems. Typically, many people do not consume enough magnesium in their diets.

Calcium, on the other hand, is the most abundant mineral in the human body. Of the calcium contained in the average body, about 99% is located in the bones, including the teeth. Calcium is needed to form bones and teeth and is also required for blood clotting, transmission of signals in nerve cells, and muscle contraction. Calcium supplementation is believed to reduce the incidence of osteoporosis.

Choosing a form of magnesium and/or calcium for supplementation has been a source of some confusion in the industry. Calcium carbonate is one form of calcium that is widely used, but is not believed to be absorbed as well as some other forms. Calcium citrate provides a form that is believed to be better absorbed than calcium carbonate. Calcium citrate/malate (CCM) is believed to be absorbed more fully than carbonate as well.

Other divalent minerals, such as zinc, copper, iron, and manganese, are also known to be important to the human diet, and can be administered in a supplemental form. For example, the trace mineral zinc is known to be involved in the transport of vitamin A, taste, wound healing, and fetal development. Zinc also plays a part in the correct functioning of many enzymes, hormones including insulin, genetic material, and proteins. Copper, on the other hand, plays a role in the absorption of iron, and is part of many enzymes. Additionally, iron is necessary for production or hemoglobin and oxygenation of red blood cells, builds up blood quality, and increases resistance as well as increasing energy production. Benefits of manganese include improvement of memory and reflexes, reducing of fatigue, and promoting proper development of thyroid hormones, skeletal, reproductive, and central nervous systems.

Malic acid is a dicarboxylic acid that is naturally occurring. Malic acid plays a role in the complex process of deriving ATP (the energy currency that runs the body) from food. Malic acid is found in a wide variety of fruits (including richly in apples) and vegetables. As malic acid is already found abundantly in humans and other warm-blooded animals, it can be administered without adverse affects. Further, there is some evidence that malic acid supplementation can be helpful to human nutrition.

SUMMARY OF THE INVENTION

It has been recognized that the use of certain complexes can provide a quantity of a bioavailable form of certain nutritionally relevant metals. Specifically, a composition meeting this criterion can have the structure:

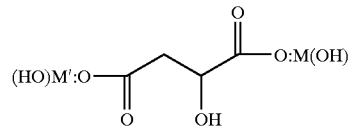

Formula 1 wherein M and M' are each independently a nutritionally relevant divalent metal.

Additionally, a method of administering a high content of a divalent essential metal in a bioavailable form to a warm-blooded animal is also provided. The method comprises the step of administering the composition of Formula 1 to a warm-blooded animal.

In another embodiment, a method of making a bioavailable divalent metal-containing complex, such as that shown in Formula 1, can comprise the step of reacting malic acid with a divalent metal-containing composition at a 1:2 molar ratio, wherein the divalent metal of the divalent metal-containing composition is a nutritionally relevant divalent metal.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It is to be noted that, as used in this specification and the appended claims, the singular forms "a," "an," and "the" include plural referents unless the context clearly dictates otherwise.

The term "nutritionally relevant metal" or "nutritionally relevant divalent metal" means any divalent metal that can be used as part of a nutritional supplement, is known to be beneficial to humans and other warm-blooded animals, and is substantially non-toxic when administered in traditional amounts, as is known in the art. Examples of such metals include copper, zinc, manganese, iron, magnesium, calcium, and the like.

When referring to a dimetalhydroxy malate (such as dicalciumhydroxy malate, dimagnesium malate, etc.), the "di" portion of the name refers to two $^+M(OH)$ or metalhydroxy groups, one being complexed to a first carboxyl group of the malate ion, and the other being complexed to a second carboxyl group of the malate ion. Thus, each metal is complexed to the malate ion and is also complexed to its own hydroxy group to charge balance the metal. The metals that can be used include divalent nutritionally relevant metals, and two of the same metal or two different metals can be present at each carboxyl group of the malate ion.

The term "divalent metal-containing composition" shall mean compositions used to react with malic acid to form a dimetalhydroxy malate in accordance with embodiments of the present invention, wherein the metal can be two of the same metal, or two different metals. Elemental divalent metals, divalent metal hydroxides, divalent metal oxides, and divalent metal carbonates are included.

In one embodiment of the present invention, a composition having the structure:

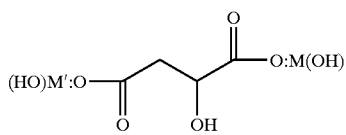

Formula 1 is provided, wherein M and M' are each independently a nutritionally relevant divalent metal. In other words, M and M' can be the same divalent metal, or can be different divalent metals. Though any nutritionally relevant divalent metal can be used, calcium, magnesium, copper, zinc, manganese, and iron provide examples of desired metals for use.

The present invention is also drawn toward a method of administering a high content of a metal in a bioavailable form to a warm-blooded animal. In one embodiment, the composition of Formula 1 above can be administered to the warm-blooded animal, such as a human. The administration can be by one of many known administration routes, including oral administration. If formulated for oral delivery or consumption, such a composition can be incorporated into many delivery vehicles, including tablets, capsules, foods, drinks, dry drink mixes, or other substances acceptable for oral consumption. Tablets may be chewable or non-chewable. A food delivery vehicle may be, for example, in the form of food bars or incorporated into dairy products. Drinks may be in the form of sports drinks, fruit drinks, citrus drinks, carbonated drinks, and other suitable drink mediums. Dry drink mixes may be in the form of a fruit mix and/or citrus mix or other particulate drink mixes. No matter what the vehicle of delivery, the compositions of the present invention are very stable, and thus, can be coadministered with many other supplements known in the art. For example, the compositions of the present invention can be coadministered with mineral salts and/or mineral amino acid chelates in drink mixes, supplement tablets or capsules, or food items.

In another embodiment, a method of making a bioavailable divalent metal-containing complex can comprise the step of reacting malic acid with one or more divalent metal-containing compositions at a 1:2 molar ratio, wherein the divalent metal of the composition is a nutritionally relevant divalent metal. This can be done in the presence of excess water, or can be done by providing a particulate blend of the malic acid and the divalent metal-containing composition, and then adding small amounts of water stepwise. The bioavailable divalent metal-containing complex formed can comprise the structure of Formula 1 above.

There are at least four specific reaction schemes that can be followed in carrying out the method of making the composition of Formula 1, though these reaction schemes are not intended to be limiting. A first reaction scheme is depicted below in Formula 2, as follows:

Formula 2

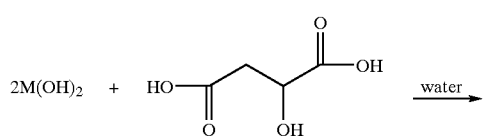

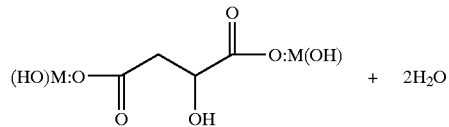

+ 2H$_2$O

In the above reaction scheme, M can be any nutritionally relevant divalent metal, including iron, magnesium, calcium, magnesium, zinc, or copper. Two extra water molecules are formed as the hydrogen atoms are liberated from the malic acid and react with the excess hydroxy groups from the two metal hydroxides. A second reaction scheme is depicted below in Formula 3, as follows:

Formula 3

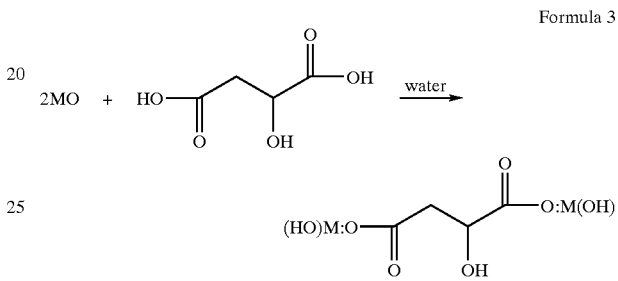

In the above reaction scheme, M can be any nutritionally relevant divalent metal, including iron, magnesium, calcium, magnesium, zinc, or copper. When a metal oxide is used, no extra water molecules are formed as in Formula 2 above. In a third reaction scheme, Formula 4 is provided as follows:

Formula 4

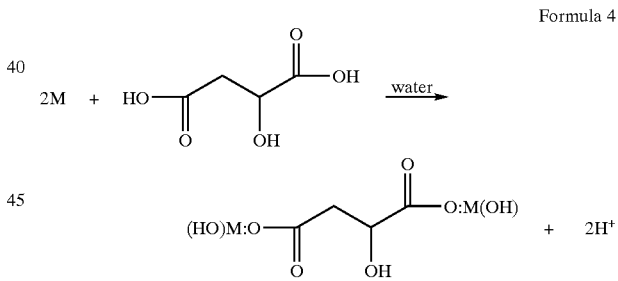

+ 2H$^+$

In the above reaction scheme, M can be any nutritionally relevant divalent metal, including iron, magnesium, calcium, magnesium, zinc, or copper. When an elemental metal is used, the extra oxygen atoms that are present in the resulting product come from the water, and two hydrogen atoms remain, either to remain in ionic form in the water, or to form H$_2$ gas. Formula 5 provides a fourth reaction scheme that can be used in preparing the compositions of the present invention, as follows:

Formula 5

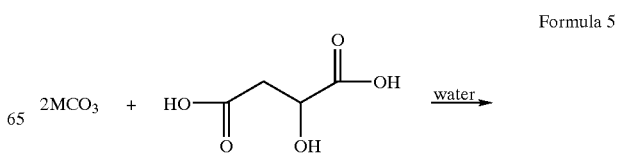

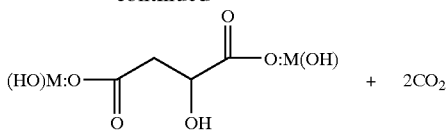 + $2CO_2$

In the above reaction scheme, M can be any nutritionally relevant divalent metal, including iron, magnesium, calcium, magnesium, zinc, or copper. When a metal carbonate is used, two carbon dioxide molecules are formed.

Though each of the reaction schemes of Formulas 2–5 are provided such that a single metal (M) is used in the reaction, combinations of any two metals can also be present on a single malate ion. In other words, by modifying the reaction schemes to include two different compositions of metal oxides, hydroxides, carbonates, or elemental metals, such compositions can be formed as would be apparent to one skilled in the art after considering the present disclosure. For example, in one embodiment, rather than using 2 molar equivalents of calcium hydroxide in the reaction scheme of Formula 2, one can use one molar equivalent of calcium hydroxide and one molar equivalent of zinc hydroxide to obtain such a result. If such a composition were prepared, three possible compositions could be present in the preparation, including 1) dicalciumhydroxy malate, 2) dizinchydroxy malate, and 3) calciumhydroxy zinchydroxy malate. Examples of the preparation of compositions having one type of metal at both carboxyl groups of the malate ion, or two different metals at each carboxyl group of the malate ion will be provided below.

With respect to each of the compositions and methods of the present invention, once formed in an aqueous solution, the product can be dried to form a particulate composition. Desired particulate sizes can be formed using one of a number of drying methods, including spray drying, drum drying, tray drying, tunnel drying, freeze drying, compressed air drying, and oven drying, among others as is known in the art.

In the above Formulas 2–5, the reactions shown are in the presence of excess water, which can be followed by a drying step. However, the same reaction schemes can be prepared in the absence of excess water. In other words, small amounts of water can be added incrementally to the reactants to form a granular product, thereby removing the need for a spray-drying step (or other equivalent drying step), if a dried product is desired. For example, the reacting step can be carried out by (a) dry blending particulate malic acid and a particulate divalent metal-containing composition to form a particulate blend; (b) adding water to the particulate blend in an amount that causes a partial reaction between the malic acid and the divalent metal-containing composition, (c) allowing the particulate blend to substantially react in the presence of the amount of water; and (d) repeating step (b) and step (c) until a granular product is formed that is substantially fully reacted.

In one embodiment, this process can be carried out by first, combining the reactants, i.e., malic acid and divalent metal-containing composition, in dry form and mixing them together, such as in a Ribbon Blender or the like. The mixing device can be continuously run during this process for acceptable results. A fraction of the total amount of water needed to effectuate the reaction can then be slowly added, such as by spraying the water into the particulate mixture. The water is preferably sprayed, as dumping water onto the reactants tends to cause over reaction and clumping. In one embodiment, from 5% to 20% of the water necessary to complete the reaction can be added or sprayed on at a time, allowing reaction time to occur between each further water addition. A water jacket can be used with the reaction vessel to keep the reactants cool.

As the water is added in small amounts stepwise, the product will progress toward completion. At each stage of added water, the reactants tend to become sponge-like and raise in level within the mixer. When the reaction nears completion for a given stage, the heat lowers, the product level falls, and the density increases, returning the product to a more granular state. Next, more water is added, and a similar phenomenon reoccurs (typically to a lesser extent at each water addition step). At each stage, the product should be allowed to react until the reaction is substantially complete. Once the heat and expansion is substantially absent when water is added, the process is done. At this point, if water is continued to be added, the product will begin to change back to a powder form, which is undesirable. Therefore, care should be taken to stop adding water when desired granulation is present, and the reaction has substantially stopped. Upon completion of the process, the product can be removed from the mixing device, stored in either a cool or warm room for drying, and optionally, ground to a desired particle size.

EXAMPLES

The following examples illustrate embodiments of the invention that are presently known. Thus, these examples should not be considered as limitations of the present invention, but are merely in place to teach how to make the best-known compositions of the present invention based upon current experimental data. As such, a representative number of compositions and their method of manufacture are disclosed herein.

Example 1

An aqueous solution of malic acid was prepared by mixing 14.79 g of malic acid with 25 mL of water until the solution was clear. An aqueous solution of calcium hydroxide was also prepared in a separate container by thoroughly mixing 16.34 g of calcium hydroxide in 25 mL of water. The calcium hydroxide solution was then added to the malic acid solution. The resulting product was a dicalciumhydroxy malate-containing solution having a slight yellow color.

Example 2

An aqueous solution of malic acid was prepared by mixing 134.09 g of malic acid with 25 mL of water until the solution was clear. Next, 112.18 g of particulate calcium oxide was slowly added to the aqueous mixture while stirring. The aqueous mixture was stirred for 45 minutes and then spray dried. The resulting product was a dicalciumhydroxy malate powder.

Example 3

A large batch of dicalciumhydroxy malate was produced by mixing 19.16 kg of malic acid in 68.19 L of water. In a separate tank, 16.33 kg of calcium oxide was mixed in 68.19 L of water. The two solutions were slowly mixed together and stirred. A milky solution containing the product resulted, which was spray dried to obtain a powdered product of dicalciumhydroxy malate.

Example 4

An aqueous solution of malic acid was prepared by mixing 134.09 g of malic acid with 50 mL of water. An aqueous solution of calcium carbonate was also prepared in a separate container by thoroughly mixing 200.18 g of calcium carbonate in 50 mL of water. The calcium carbonate solution was then slowly added to the malic acid solution. The resulting solution was spray dried to produce a powdered dicalciumhydroxy malate.

Example 5

An aqueous solution of malic acid was prepared by mixing 5.859 kg of malic acid with 18.18 L of water until the solution was clear. An aqueous solution of magnesium oxide was also prepared in a separate container by thoroughly mixing 3.515 kg of magnesium oxide in 18.18 L of water. The magnesium oxide solution was then slowly added to the malic acid solution. The resulting solution was cooled, and then spray dried to produce a powdered dimagnesiumhydroxy malate.

Example 6

An aqueous solution of malic acid was prepared by mixing 134.09 g of malic acid with 50 mL of water. An aqueous solution of copper(II)hydroxide was also prepared in a separate container by thoroughly mixing 195.12 g of copper(II)hydroxide in 50 mL of water. The copper(II) hydroxide solution was then slowly added to the malic acid solution. The resulting solution was spray dried to produce a powdered dicopper(II)hydroxy malate.

Example 7

An aqueous solution of malic acid was prepared by mixing 134.09 g of malic acid with 50 mL of water. An aqueous solution of zinc oxide was also prepared in a separate container by thoroughly mixing 162.78 g of zinc oxide in 50 mL of water. The zinc oxide solution was then slowly added to the malic acid solution. The resulting solution was spray dried to produce a powdered dizinchydroxy malate.

Example 8

An aqueous solution of malic acid was prepared by mixing 134.09 g of malic acid with 50 mL of water. Next, 111.69 g of ferronyl powder was added to the malic acid solution. The solution was stirred for approximately 2 hours. The resulting solution was hen spray dried to produce a powdered dihydroxyferrous malate.

Example 9

An aqueous solution of malic acid was prepared by mixing 134.09 g of malic acid with 50 mL of water. Next, 109.88 g of Mn metal was added slowly to the malic acid solution. The solution was stirred for approximately 2 hours. The resulting solution was then spray dried to produce a powdered dimanganesehydroxy malate.

Example 10

An aqueous solution of malic acid was prepared by mixing 134.09 g of malic acid with 50 mL of water. An aqueous solution of zinc oxide was also prepared in a separate container by thoroughly mixing 81.39 g of zinc oxide in 50 mL of water. Next, 54.94 g of ferronyl powder was then added to the malic acid solution. The zinc oxide solution was then slowly added to the iron/malic acid solution. The solution was allowed to mix for approximately 2 hours. The resulting solution was then spray dried to produce a powdered dihydroxyzinc ferrous malate (or zinc hydroxy ferrous hydroxy malate).

Example 11

An aqueous solution of malic acid was prepared by mixing 134.09 g of malic acid with 50 mL of water. An aqueous solution of calcium oxide was also prepared in a separate container by thoroughly mixing 56.08 g of calcium oxide in 50 mL of water. Next, 54.94 g of ferronyl powder was then added to the malic acid solution. The calcium oxide solution was then slowly added to the iron/malic acid solution. The solution was allowed to mix for approximately 2 hours. The resulting solution was then spray dried to produce a powdered dihydroxycalcium ferrous malate (or calciumhydroxy ferroushydroxy malate).

Example 12

An aqueous solution of malic acid was prepared by mixing 134.09 g of malic acid with 50 mL of water. An aqueous solution of calcium hydroxide was also prepared in a separate container by thoroughly mixing 74.09 g of calcium hydroxide in 50 mL of water. Next, 54.94 g of ferronyl powder was then added to the malic acid solution. The calcium hydroxide solution was then slowly added to the iron/malic acid solution. The solution was allowed to mix for approximately 2 hours. The resulting solution was then spray dried to produce a powdered dihydroxycalcium ferrous malate (or calciumhydroxy ferroushydroxy malate).

Example 13

An aqueous solution of malic acid was prepared by mixing 134.09 g of malic acid with 50 mL of water. An aqueous solution of calcium carbonate was also prepared in a separate container by thoroughly mixing 100.09 g of calcium carbonate in 50 mL of water. Next, 54.94 g of ferronyl powder was added to the malic acid solution. The calcium carbonate solution was then slowly added to the iron/malic acid solution. The solution was allowed to mix for approximately 2 hours. The resulting solution was then spray dried to produce a powdered dihydroxycalcium ferrous malate (or calciumhydroxy ferroushydroxy malate).

Example 14

An aqueous solution of malic acid was prepared by mixing 134.09 g of malic acid with 50 mL of water. An aqueous solution of zinc oxide was also prepared in a separate container by thoroughly mixing 81.38 g of zinc oxide in 25 mL of water. An aqueous solution of calcium oxide was also prepared in a separate container by thoroughly mixing 56.08 g of calcium oxide in 25 mL of water. The zinc oxide solution and the calcium oxide solution were then slowly added to the malic acid solution. The resulting solution was then spray dried to produce a powdered dihydroxycalcium zinc malate (or calciumhydroxy zinchydroxy malate).

Example 15

An aqueous solution of malic acid was prepared by mixing 134.09 g of malic acid with 50 mL of water. An aqueous solution of zinc oxide was also prepared in a separate container by thoroughly mixing 81.38 g of zinc oxide in 25 mL of water. An aqueous solution of calcium hydroxide was also prepared in a separate container by thoroughly mixing 74.09 g of calcium hydroxide in 25 mL of water. The zinc oxide solution and the calcium hydroxide solution were then slowly added to the malic acid solution. The resulting solution was then spray dried to produce a powdered dihydroxycalcium zinc malate (or calciumhydroxy zinchydroxy malate).

Example 16

An aqueous solution of malic acid was prepared by mixing 134.09 g of malic acid with 50 mL of water. An aqueous solution of zinc oxide was also prepared in a separate container by thoroughly mixing 81.38 g of zinc oxide in 25 mL of water. An aqueous solution of calcium carbonate was also prepared in a separate container by thoroughly mixing 100.09 g of calcium carbonate in 25 mL of water. The zinc oxide solution and the calcium carbonate solution were then slowly added to the malic acid solution. The resulting solution was then spray dried to produce a powdered dihydroxycalcium zinc malate (or calciumhydroxy zinchydroxy malate).

Example 17

A dicalciumhydroxy malate granular product was prepared by mixing two molar equivalents of particulate calcium hydroxide with one molar equivalent of particulate malic acid (totaling 45 kg for the entire composition) in a Ribbon Blender for 15 minutes at normal speeds. A water jacket was used to ensure that the product would not over react when small amounts of water were added to the batch. Next, about 1 L of water was slowly sprayed into the particulate mixture product. After about 10 minutes of reaction time (where the product became spongy and had risen, and then dropped back to a more granular state), an additional 1 L of water was added. This was repeated several times until no further reaction appeared to be occurring upon addition of water. The end result was a granular product. Once a fully reacted granular product was formed, no additional water was added. The resulting composition was then dried in a cool room and ground to a predetermined particle size.

Example 18

The same process of Example 17 was followed, except that magnesium hydroxide was used instead of calcium hydroxide. This process resulted in a granular dimagnesiumhydroxy malate.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A composition having the structure:

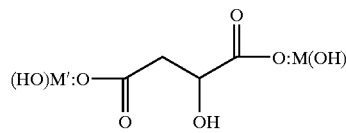

wherein M and M' are each independently a nutritionally relevant divalent metal.

2. A composition as in claim 1, wherein M is calcium.
3. A composition as in claim 1, wherein M is magnesium.
4. A composition as in claim 1, wherein M is zinc.
5. A composition as in claim 1, wherein M is copper.
6. A composition as in claim 1, wherein M is iron.
7. A composition as in claim 1, wherein M is manganese.
8. A composition as in claim 1, wherein M and M' are the same nutritionally relevant divalent metal selected from the group consisting of copper, zinc, manganese, iron, magnesium, and calcium.
9. A composition as in claim 1, wherein M and M' are different nutritionally relevant divalent metals, each being selected from the group consisting of copper, zinc, manganese, iron, magnesium, and calcium.
10. A composition as in claim 1 in a dry particulate form.
11. A method of administering a high content of a divalent essential metal in a bioavailable form to a warm-blooded animal, comprising:

administering a composition having the structure:

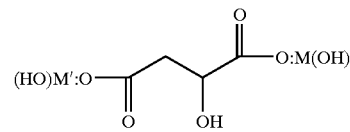

to a warm blooded animal, wherein M and M' are each independently a nutritionally relevant divalent metal.

12. A method as in claim 11, wherein M and M' are the same nutritionally relevant divalent metal selected from the group consisting of copper, zinc, manganese, iron, magnesium, and calcium.
13. A method as in claim 11, wherein M and M' are different nutritionally relevant divalent metals, each being selected from the group consisting of copper, zinc, manganese, iron, magnesium, and calcium.
14. A method as in claim 11, wherein the administering step includes coadministering a mineral salt or mineral amino acid chelate with the composition.
15. A method as in claim 11, further comprising the preliminary step of formulating the composition into a supplement tablet or capsule for oral delivery.
16. A method as in claim 11, further comprising the preliminary step of formulating the composition into a food or beverage for oral delivery.
17. A method of making a bioavailable divalent metal-containing complex, comprising reacting malic acid with one or more divalent metal-containing composition at a 1:2 malic acid to divalent metal-containing composition molar ratio, said divalent metal being one or more of a nutritionally relevant divalent metal.
18. A method as in claim 17, wherein the bioavailable divalent metal-containing complex has the structure:

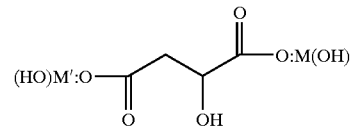

wherein M and M' are each individually the one or more nutritionally relevant divalent metal.

19. A method as in claim 17, wherein the step of reacting is by the following reaction scheme:

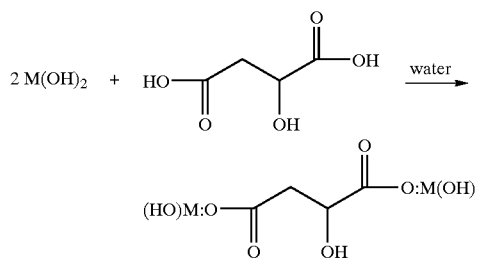

wherein M is selected from the group consisting of copper, zinc, manganese, iron, magnesium, and calcium.

20. A method as in claim 17, wherein the step of reacting is by the following reaction scheme:

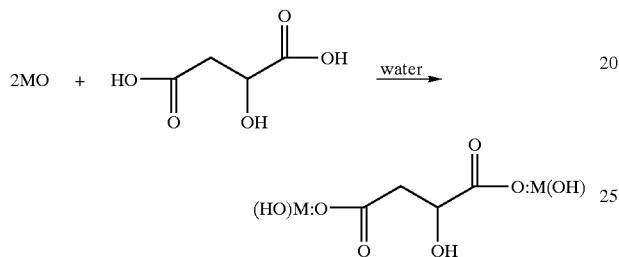

wherein M is selected from the group consisting of copper, zinc, manganese, iron, magnesium, and calcium.

21. A method as in claim 17, wherein the step of reacting is by the following reaction scheme:

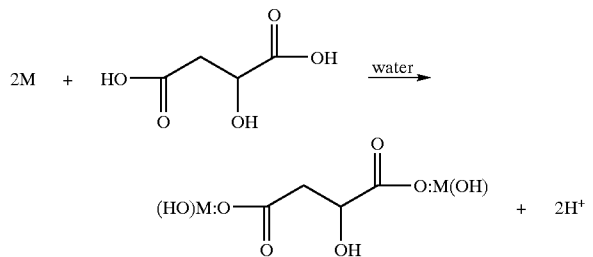

wherein M is selected from the group consisting of copper, zinc, manganese, iron, magnesium, and calcium.

22. A method as in claim 17, wherein the step of reacting is by the following reaction scheme:

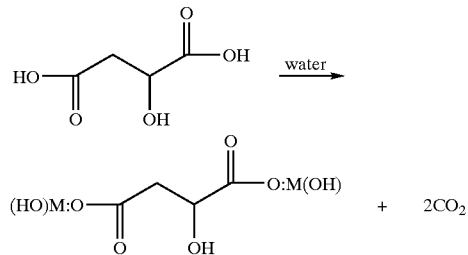

wherein M is selected from the group consisting of copper, zinc, manganese, iron, magnesium, and calcium.

23. A method as in claim 17, wherein the reacting step is carried out in excess water, followed by a drying step to form a particulate composition.

24. A method as in claim 17, wherein the reacting step is carried by (a) dry blending the malic acid and the divalent metal-containing composition to form a particulate blend;

(b) adding water to the particulate blend in an amount that causes a partial reaction between the malic acid and the divalent metal-containing composition, (c) allowing the particulate blend to substantially react in the presence of the amount of water; and (d) repeating step (b) and step (c) until a granular product is formed that is substantially fully reacted.

25. A method as in claim 24, further comprising the step of allowing the granular product to dry.

26. A method as in claim 25, further comprising the step of grinding the granular product to form particulates of a predetermined particle size.

* * * * *